Feb. 19, 1974 W. D. HOLLEY Plant Pat. 3,487
CARNATION PLANT
Filed Aug. 16 1972
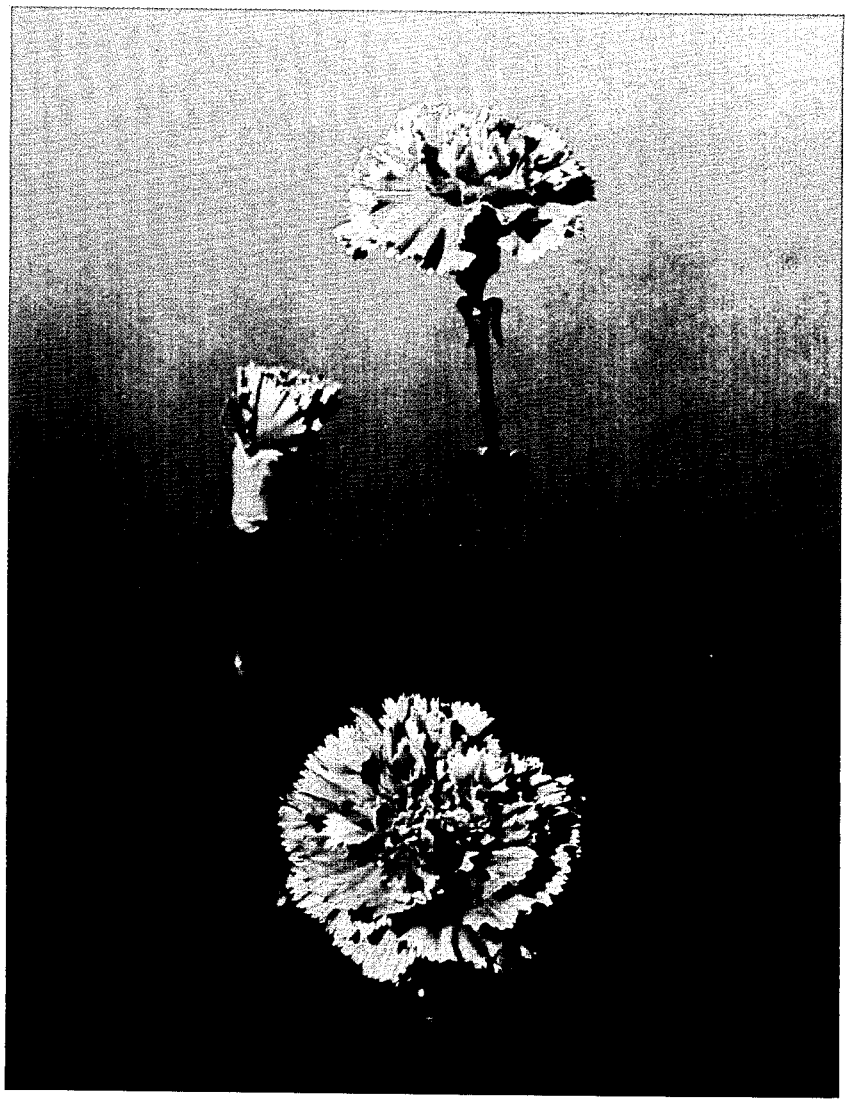

United States Patent Office

Plant Pat. 3,487
Patented Feb. 19, 1974

3,487
CARNATION PLANT

Winfred Davis Holley, Fort Collins, Colo., assignor to Colorado State University Research Foundation, Fort Collins, Colo.

Filed Aug. 16, 1972, Ser. No. 281,200
Int. Cl. A01h 5/00
U.S. Cl. Plt.—70 1 Claim

ABSTRACT OF THE DISCLOSURE

A new variety of carnation plant distinguished by its continuous and profuse production of relatively large flowers having a generally cyclamen purple color; and by its vigorous growth and rapid flowering habit resulting in an exceptionally high yield of commercial quality blossoms.

BACKGROUND OF THE NEW PLANT

My new variety of carnation plant originated as a seedling of a self-pollinated, unnamed and unpatented $F_1$ hybrid and was discovered by me in November 1967, in the course of extensive breeding efforts carried on in research greenhouses at Fort Collins, Colo., with the objective of developing plants having higher yield of high commercial quality flowers. This plant was observed to have an exceptionally rapid growth habit and an abundant production of high quality flowers. It was also noted that the lateral growth at the base of the flower stem grew with exceptional speed so that the second flower crop was almost continuous with the first.

Asexual propagation of this new variety of carnation, by cutting, has been carried on under my direction at Fort Collins, Colo., and it has been found that its flowering, from planting of rooted cuttings, is up to eight weeks sooner than similar commercial carnation varieties. Continued asexual propagation of the plant through many generations at Fort Collins, Colo., has shown that the distinctive and valuable characteristics of its growth and flowering habits are firmly fixed.

DESCRIPTION OF THE DRAWING

My new variety of carnation plant is illustrated by the accompanying drawing which photographically shows the form and color characteristics of the flower as nearly true as it is reasonably possible to obtain by conventional photographic procedures, the drawing showing a partly opened bud and side and face views of a fully opened blossom.

DESCRIPTION OF THE NEW PLANT

The following is a detailed description of the new variety of carnation plant with color designations according to the Horticultural Color Chart issued by The British Colour Council in collaboration with The Royal Horticultural Society at London, England.

*The plant*

Origin: Seedling
Parentage: An unnamed self-pollinated $F_1$ hybrid (unpatented).
Classification:
*Botanic.*—Caryophyllus
*Commercial.*—Standard greenhouse carnation
Form: Bush
Height: 36 to 40 inches at first crop. 58 to 62 inches after the first year
Growth: Vigorous and strong, with sturdy upright stems.
Branching: Much, near the base of flower stems, with exceptionally rapid growth to flowering.
Foliage: Quantity—typical for carnations.

*Size of leaf.*—1 by 15 cm. for eight leaf below the flower in summer. Somewhat larger in winter and spring
*Shape.*—Lanceolate and curled downwardly
*Texture.*—Leathery and smooth
*Color.*—Upper side—Carnation Green 00058. Under side—Carnation Green 00058
*Ribs.*—Single central rib—not prominent
*Petioles.*—None. Leaf is decurrent and amplexicaul

*The bud*

Form: Comparatively broad ovoid—urn
Size: 3 to 3½ cm. tall and 2 cm. in diameter. Somewhat larger in winter
Opening rate: Slow, depending upon temperature
Color:
*When sepals first divided.*—Cyclamen Purple 30/2 to 30/3
*When sepals unfurl.*—Cyclamen Purple 30/2 to 30/3
Sepals: Broad and stand up from calyx
*Color.*—Inside—Pea Green 61/3. Outside—Agathia Green 60/1
Calyx: Urn shaped and broad, with little or no splitting
*Aspect.*—Distinctly ribbed

*The flower*

Blooming habit: Profuse and continuous
Size of bloom: Large, 8 to 10 cm. in diameter and 4 to 5 cm. in depth
Borne: Singly, after disbudding
Shape: High center, with flat outer petals
Petalage: 60 to 70 petals in a whorl arrangement
*Form.*—Typically carnation with medium serration and frilly apex
*Color.*—Outer petal—Cyclamen Purple 30/2 to 30/3 over main area and 30 at base. Inside petal—Cyclamen Purple 30. Reverse side—Cyclamen Purple 30/2 to 30/3. Apex margins have lighter color often stippled with white. In some cases, petal ends may have white or near white bands up to 1 cm. wide
Effect of weather: Blooms are smaller in hot weather
Fragrance: Distinctly fragrant
Persistence: Flowers hang on and dry
Lasting Quality:
*On plant.*—7 to 10 days
*As cut flowers.*—7 to 14 days

*Reproductive organs*

Stamens:
*Anthers.*—Scattered in center petals. Number varies from 5 to 10. Color: Unopened—Wisteria Blue 640/2
*Filaments.*—Length—about 2 cm. Color: White
*Pollen.*—Color—Wisteria Blue 640/3
Pistils: 1, branched to about 3 cm. in length at maturity
Stigmas: Color—Wisteria Blue 640/2 and whiter
Ovaries: Normal, 5-lobed

*Fruit*

A 5-lobed, straw colored capsule, normally producing few, if any, slightly fertile seeds.

This new variety of carnation plant is of the same color class as Orchid Beauty (P.P. 193) and Safari (unpatented) with the color markings more closely resembling those of Orchid Beauty. My new variety is distinguished, however, in that the petal edges have a white stippling, that make them of whiter appearance than those of Orchid Beauty, and very often the petals of the new plant have margins of white or near white up to one cm. wide.

My new variety of carnation is also distinguished from Orchid Beauty by its much more rapid flowering, from the time of planting rooted cuttings, and by the extremely rapid growth of the lateral branches which appear at the base of the flower stems so that the second crop of flowers is almost continuous with the first crop. It is this growth habit which contributes materially to the high yield capabilities of this new plant.

My new carnation is distinguished from Safari by its faster growth, taller plant and a somewhat different flower color. Safari has a similar ground color in its flower petals but much more white stippling throughout the petal surface. The basal half or more of the petals of my new variety are of a solid cyclamen purple color.

I claim:

1. A new and distinct variety of carnation plant, substantially as herein shown and described, characterized by its tall, vigorous and very rapid growth habit and early flowering, by the extremely rapid growth of the laterals appearing at the base of the flower stems as the first flowers appear, and by its high yield of large commercial quality flowers.

No references cited.

ROBERT E. BAGWILL, Primary Examiner